United States Patent [19]
Fuchs

[11] Patent Number: 5,752,917
[45] Date of Patent: May 19, 1998

[54] NETWORK CONNECTIVITY FOR A PORTABLE PATIENT MONITOR

[75] Inventor: Kenneth Fuchs, Wayland, Mass.

[73] Assignee: Siemens Medical Systems, Inc., Iselin, N.J.

[21] Appl. No.: 618,157

[22] Filed: Mar. 19, 1996

[51] Int. Cl.⁶ .................................................. A61B 5/02
[52] U.S. Cl. ....................................................... 600/484
[58] Field of Search ................................... 128/630, 670, 128/671, 687, 672, 736, 716, 633; 340/573; 600/300, 301, 310, 484, 529

[56] References Cited

U.S. PATENT DOCUMENTS

| | | | |
|---|---|---|---|
| 4,216,462 | 8/1980 | McGrath et al. | 340/150 |
| 4,804,950 | 2/1989 | Moon et al. | 340/715 |
| 4,895,161 | 1/1990 | Cudahy et al. | 128/630 X |
| 4,916,441 | 4/1990 | Gombrich | 340/712 |
| 5,375,604 | 12/1994 | Kelly et al. | |
| 5,441,047 | 8/1995 | David et al. | 128/630 X |
| 5,469,844 | 11/1995 | Rogler | 128/630 |

FOREIGN PATENT DOCUMENTS

| | | |
|---|---|---|
| 0 553 372 A1 | 1/1992 | European Pat. Off. |
| 0 735 499 A1 | 2/1995 | European Pat. Off. |
| 0 261 927 A2 | 9/1997 | European Pat. Off. |
| WO 93/01574A | 7/1992 | WIPO |
| WO 94/24929A | 4/1993 | WIPO |

*Primary Examiner*—Jennifer Bahr
*Assistant Examiner*—Samuel Gilbert
*Attorney, Agent, or Firm*—Lawrence C. Edelman

[57] ABSTRACT

A monitor system for acquiring medical data from a patient is distributed over at least two geographically separate patient monitoring areas and interconnected via a communication network. A portable monitor (102) coupled to a patient receives and processes patient data signals from a sensor coupled to the patient. At least two patient monitor docking stations (111) are provided, each one of which is selectively coupled to the portable monitor and connected for transmission of patient data received from the portable patient monitor to the communication network. Each docking station comprises a coupler for detachably coupling the portable monitor to the docking station, a signal transfer device (108) for transferring patient-related data signals between the portable monitor and the docking station when the portable monitor is coupled to the docking station, and a signal processor for monitoring the patient-related data signals provided by the signal transfer device for developing a connection information signal when the portable monitor is coupled to the docking station, the connection information signal being applied for developing an alarm in the event that the signal processor monitors that the portable monitor is not operating correctly.

11 Claims, 3 Drawing Sheets

NETWORK CONNECTIVITY FOR A PORTABLE PATIENT MONITOR

FIELD OF THE INVENTION

The present invention relates to network systems, and in particular to a networked portable patient monitoring system for collecting, storing, and displaying medical data.

BACKGROUND OF THE INVENTION

In hospitals and other health care environments, it is often necessary to substantially continuously collect and analyze a variety of medical data from a patient. These data may include electrocardiogram, temperature, blood pressure, respiration, pulse and other parameters.

Patient monitoring systems have typically fallen into one of two general categories: multi-function monitoring, recording and displaying systems which process and collect all of the data desired, but are bulky and difficult to transport; and small, portable systems which are easy to transport, but process and collect fewer types of data and have limited storage capability.

The need for continuity of data collection and display is most pressing in emergency situations. During an emergency, the speed at which a patient is transferred from an ambulance to an emergency room, or from a bed to an operating room or intensive care unit may substantially impact the patient's chance of survival. Not only is it is important to provide a similar level of monitoring during transport as was provided during stationary applications, but it is also desirable from a clinical point of view to provide a substantially continuous monitoring capability and data history availability which follows the patient.

In accordance with the above desires, U.S. Pat. No. 5,375,604, entitled TRANSPORTABLE MODULAR PATIENT MONITOR, assigned to the same Assignee as the present invention, describes a transportable patient monitoring system of the type including at least two docking stations, one located at each of two geographically distributed areas, either of which physically and electrically supports a transportable patient monitor. Each docking station also provides a connection to a hospital communication network for transfer of patient related data between the portable monitor and the network.

Although the system described in the '604 patent is a vast improvement over the prior art, further improvement is desirable. For example, each patient care area is equipped with at least one node or connection point for connecting the docking station to the hospital network for allowing transfer of patient related information therebetween. Typically, a central monitoring or nurses station (or workstation) is also coupled to the node of the network for allowing a user (a nurse or physician) to monitor the patient from a remote location.

However, since patient monitoring is a critical function, hospital networks are typically set up to provide an alarm to the monitor user whenever there is an unexpected loss of the receipt of the patient data. Note, this alarm is in addition to the conventional alarm generated by the monitor when a monitored parameter exceeds a preset threshold or alarm limit. Unfortunately, in a portable patent monitoring system, if a patient monitor is attached directly to a communications network at a node by the patient's bed, and is then detached, for example when the patient is to be moved to another location, any monitor, central station or workstation monitoring the patient at that bed will detect the sudden loss of patient data as an error condition and create a false alarm.

It is desirable to have a networked portable patient monitoring system in which portable monitors can be easily disconnected from the network without sacrificing the alarm features of the monitoring system.

Furthermore, it would be desirable that such easy disconnection for portable monitors be provided in a simple and cost effective manner.

It is an object of the present invention to provide such a networked portable patient monitoring system.

SUMMARY OF THE INVENTION

A monitor method and apparatus for acquiring medical data from at least one sensor adapted for attachment to a patient. The apparatus is distributed over at least two geographically separate patient monitoring areas via a communication network having at least one network node connection in each of said areas. The apparatus comprises a portable monitor adapted for coupling to the sensor, for receiving and processing patient data signals acquired from the sensor when said sensor is attached to the patient. The apparatus also includes a patient monitor docking station in electrical communication with the network and located in each of the at least two patient monitoring areas for transmission of patient data between the patient monitors and the communication network. Each docking station comprises; coupling means for detachably coupling the portable monitor to the docking station; first transfer means for transferring monitor information signals including patient data between the portable monitor and the docking station when the portable monitor is coupled to the docking station; and signal processing means, responsive to said information signals for developing a connection information signal which is used to develop an alarm in the event that the signal processing means monitors that said portable monitor is not operating correctly.

DETAILED DESCRIPTION OF THE EXEMPLARY EMBODIMENT

Figure 1:
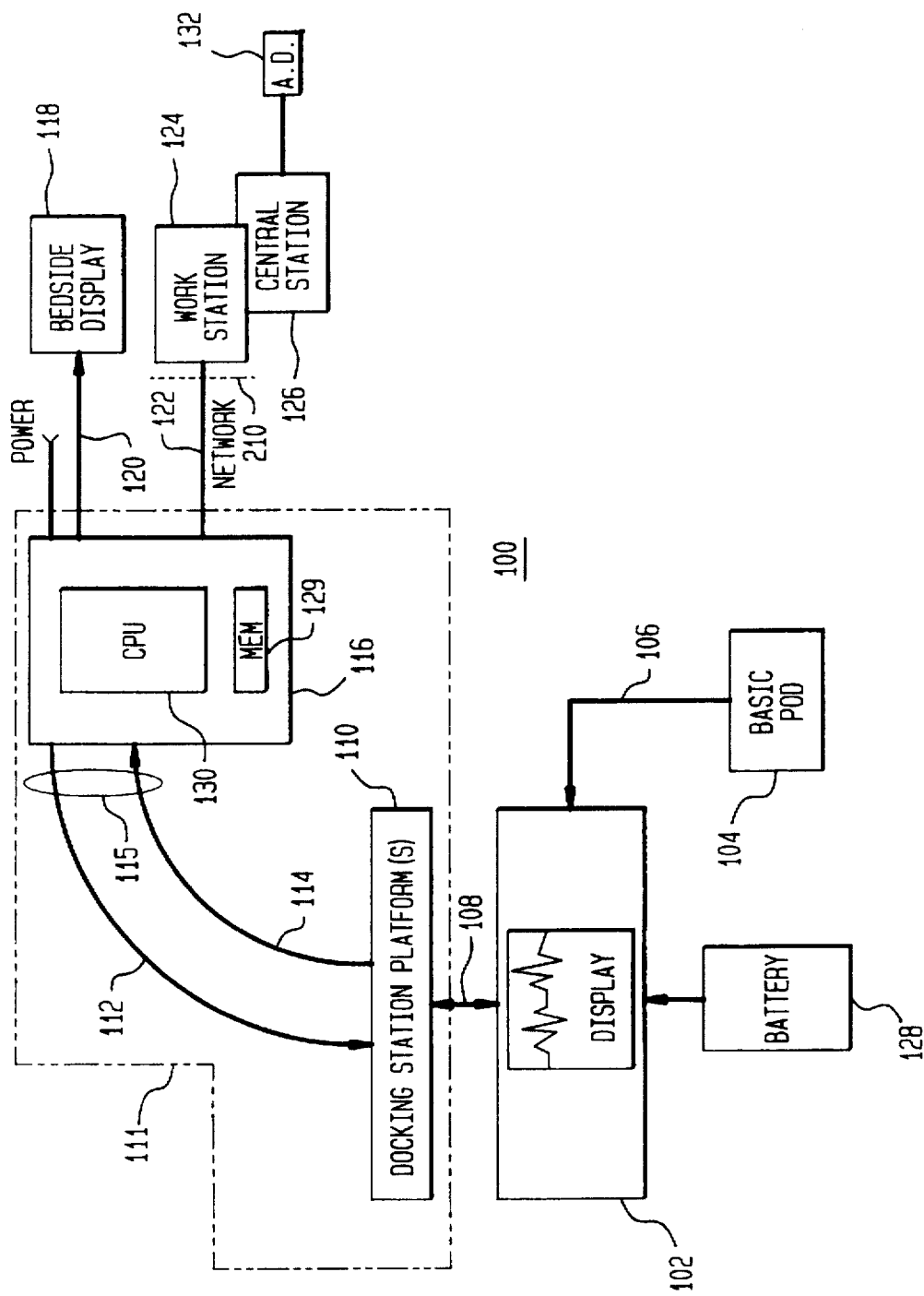
FIG. 1 illustrates in block diagram form a patient monitoring system constructed in accordance with the present invention.

FIG. 1 illustrates an exemplary networked portable patient monitoring system 100 including a docking station 111 for connecting a portable monitor to a network in accordance with the present invention. A portable monitor 102 acquires physiological data signals from a plurality of sensors (not specifically shown), which may include both invasive and non-invasive devices, for collecting physiological data from a patient. In the illustrated embodiment a basic pod 104 is provided in a housing remote from portable monitor 102 for acquiring ECG, SpO2 and Temperature data from a plurality of appropriate sensors connected to the patient, and providing this data to monitor 102 via a single detachable cable 106. Portable monitor 102 will typically display the physiological data, and also transmit patient-related data signals to docking station 111 via a connection 108. (It will be understood by one skilled in the art that the term "patient-related data", as used herein, may refer to the processed physiological information derived from the signals produced by sensors associated with pod 104, as well as signals for providing status and control information to other devices in the monitoring system).

Docking station 111 provides power and communications services to portable monitor 102 during the time that monitor 102 is mounted on and in electrical communication with the docking station. The mounting mechanism, as will be described in detail later on, provides for rapid connection/ disconnection of monitor 102 from docking station 111 (both mechanically and electrically) for transport. Preferably, the connection/disconnection is accomplished in a single step, so that the user can easily "pick-up and go" with monitor 102, easily and rapidly transporting it from one location to another location in the monitoring system, without handling any individual cables or connectors.

Docking station 111 includes two modular components. The first component is a docking station platform 110. Portable monitor 102 may be placed on any one of a plurality of docking station platforms 110, which are typically distributed throughout the hospital in various patient care areas (Emergency room, ICU's, CCU's, etc.), and positioned, for example, near the patient's bed or attached to the bedframe. Docking station platform 110 provides both mechanical support for portable monitor 102, as well as electrical support, i.e., a connection 112 to a source of operating power and a connection 114 for transfer of acquired patient related data from portable monitor 102 to other devices. Connections 112 and 114 are typically included as part of a link or cable 115.

The second component of the docking station is a power supply and network box 116 referred to herein as wallbox 116, for completing the electrical connections provided by docking station platform 110. That is, wallbox 116 provides a source of operating power to connection 112 as well as providing for the transfer of the patient-related data to the other devices. Such transfer can comprise, e.g., a connection to a bedside display 118 via a direct connection 120, and a network connection (node) 122 for connection to a care unit network 210 (Local Area Network, LAN). Node 122 provides for transfer of the patient-related data to other devices connected to the network at other ones of the network nodes, such as a network connected intelligent workstation 124 or central station 126. Additional direct and network connections are possible for wallbox 116, but are not shown for the sake of brevity.

In the FIG. 1 embodiment, wallbox 116 is physically included in docking station 111. In an alternative embodiment shown in FIG. 2, wallbox 116 is referred to as a power supply and network box (PSN) 216, which is physically separate from docking station platform 110, and is coupled to docking station platform 110 via cable 115. In either embodiment, the functions provided by wallbox 116 and PSN 216 are very similar, and throughout the description this should be kept in mind. In either embodiment, wallbox 116 provides both power for operating monitor 102 (and for charging a battery pack 128 within, or attached to, monitor 102) and provides communications links to networks and devices, both inside and outside of the room in which docking station 111 is located.

Thus, docking station 111 provides a simple mechanism to connect portable monitoring devices with several other devices and networks without the need to connect individual cables for each device or network. Data and power connectors on the docking station platform 110 and on the cases of the portable devices allow simultaneous physical and electrical couplings to be established.

Portable monitor 102 is a self-contained, standalone monitoring system. Monitor 102 also includes all of the processing electronics necessary to process, display and store patient data during transport. In the exemplary embodiment described herein, portable monitor 102 does not include a broad suite of network interfaces; during transport, the exemplary monitor 102 does not have any connections to a central monitoring system or to communications networks, however wireless transmitting/ receiving circuitry could be included in monitor 102 in order to provide network capability during transport.

As shown and described so far the system is substantially similar to the system shown and described in detail in Assignee's forenoted U.S. Pat. No. 5,375,604, incorporated herein by reference. For further details of this system, the reader should refer to this patent.

In accordance with the principles of the present invention wallbox 116 includes a network interface processor 130. Processor 130 is coupled at its input to the electrical connection 114 (the communication link provided by cable 115 of FIG. 2) for monitoring the patient data signals provided by portable monitor 102, and has an output coupled to network node 122. Processor 130 comprises a central processing unit (CPU) and a memory 129 (ROM/RAM) which periodically (e.g., each 10 seconds) provides a name service to node 122 for distribution to other devices on the network, such as workstation 124 and the central monitoring station 126, as well as a connection information signal indicative of the proper connection and/or proper removal or loss of signal from a portable monitor 102, such as "NODE 122/ CCU 3/UNIT 4/BED 2/ALL OK (or, MONITOR 56/with some patient related data, such as a portion of an EKG waveform)". This connection information signal is then communicated to the network along with the name service information for distribution to other devices on the network, such as the central monitoring station 126, where an alarm device 132 can be activated in the event that the signal is indicative of an improper loss of signal or improper connection/disconnection of a portable monitor. For example, processor 130 can monitor the communication link (cable 115) between it and patient monitor 102. If monitor 102 looses power (e.g., it's battery becomes exhausted), or if communications are unexpectedly disrupted (for example do to a partial electrical disconnection between monitor 102 and platform 110), processor 130 can communicate this dangerous condition to the rest of the monitoring network via wallbox 116. In this case, wallbox 116 provides a connection information signal on network node 122 which will identify the node and alarm this condition. If, on the other hand, the monitor has intentionally been removed by the user from the platform 110 for initiating a patient transport (pick and go), then processor 130 can also recognize this event and provide information to the network that indicates that a monitor 102 has been removed from the docking station at node 122 and that no alarm notification is required.

Figure 3:
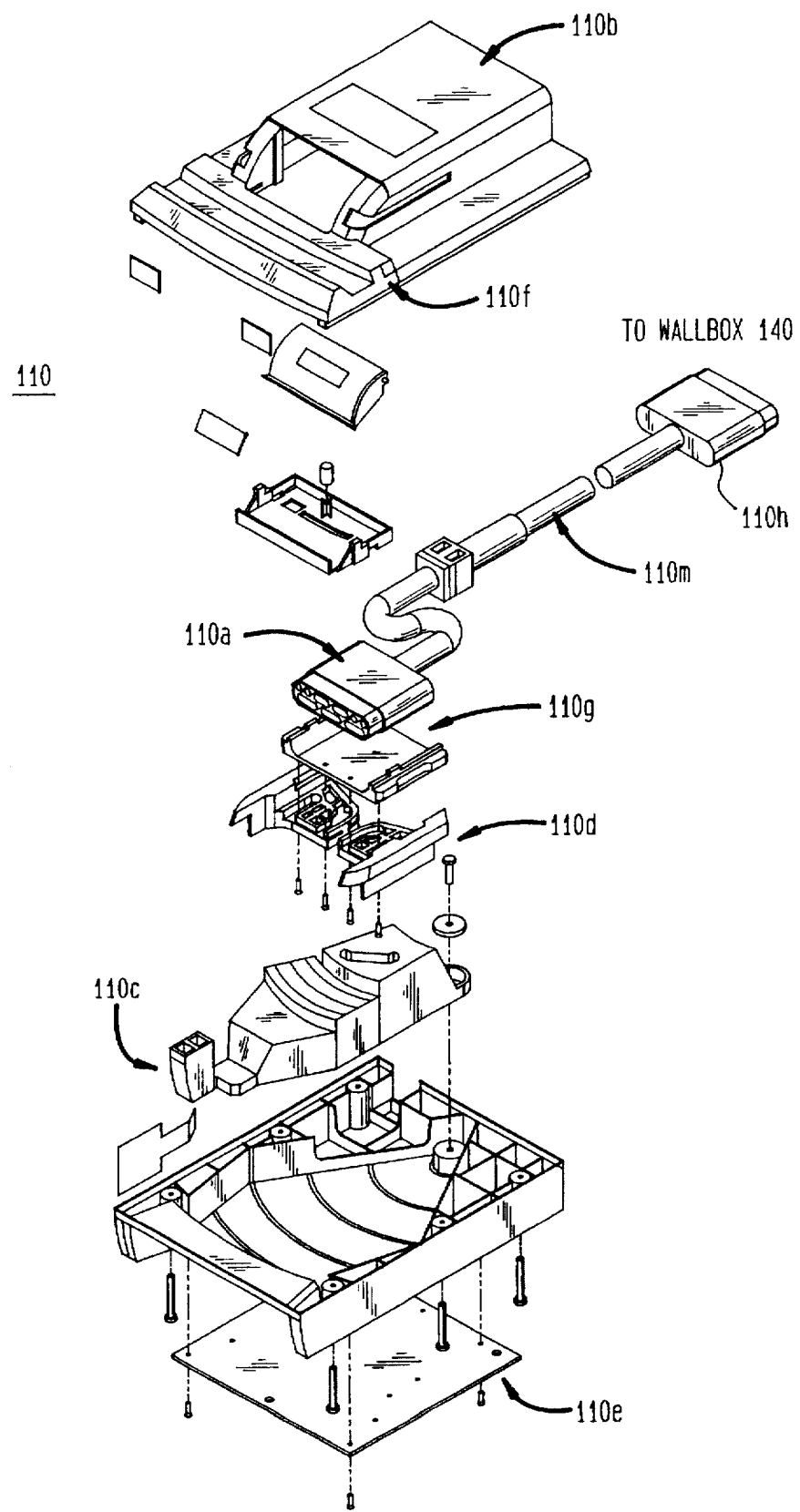
FIG. 3 illustrates an exploded view of the docking station platform shown in FIG. 2.

More specifically, processor 130 can monitor the individual messages or signals in the communication link between it and patient monitor 102, which link is shown and described in more detail in FIG. 3, to detect not only the proper connection of a portable monitor 102 to the docking station platform 110, in which case predetermined or expected signals are present on the link, but to also detect if the monitor has been activated or not. If the monitor has been connected but not activated, the fact that there is no patent data signals on the communication link 115 is normal, and an alarm will not be generated by processor 130.

(Alternatively, a signal can be generated and provided by processor 130 to the network indicating the name of the network node, such as bed 2 in ICU 1, and that the connection is normal.) If, on the other hand, processor 130 detects that a monitor has been incorrectly connected to the docking station, an alarm could be generated. Incorrect connection could be sensed by processor 130 by sensing, e.g., an incorrect pattern of signals in link 115. Additionally, once processor 130 detects that a monitor has been properly connected and activated, but that there is no patent data signals on communication link 115, then an alarm will be generated. Furthermore, in the event that after processor 130 detects that a monitor has been properly connected and activated, but that there is an incorrect pattern of signals in link 115, then an alarm will also be generated.

Additionally, processor 130 may provide, if needed, for the conversion of the signals on cable 115 to a format needed for network 210. Even furthermore, processor can provide an alarm signal which can be used to activate a local alarm (not specifically shown).

Figure 2:
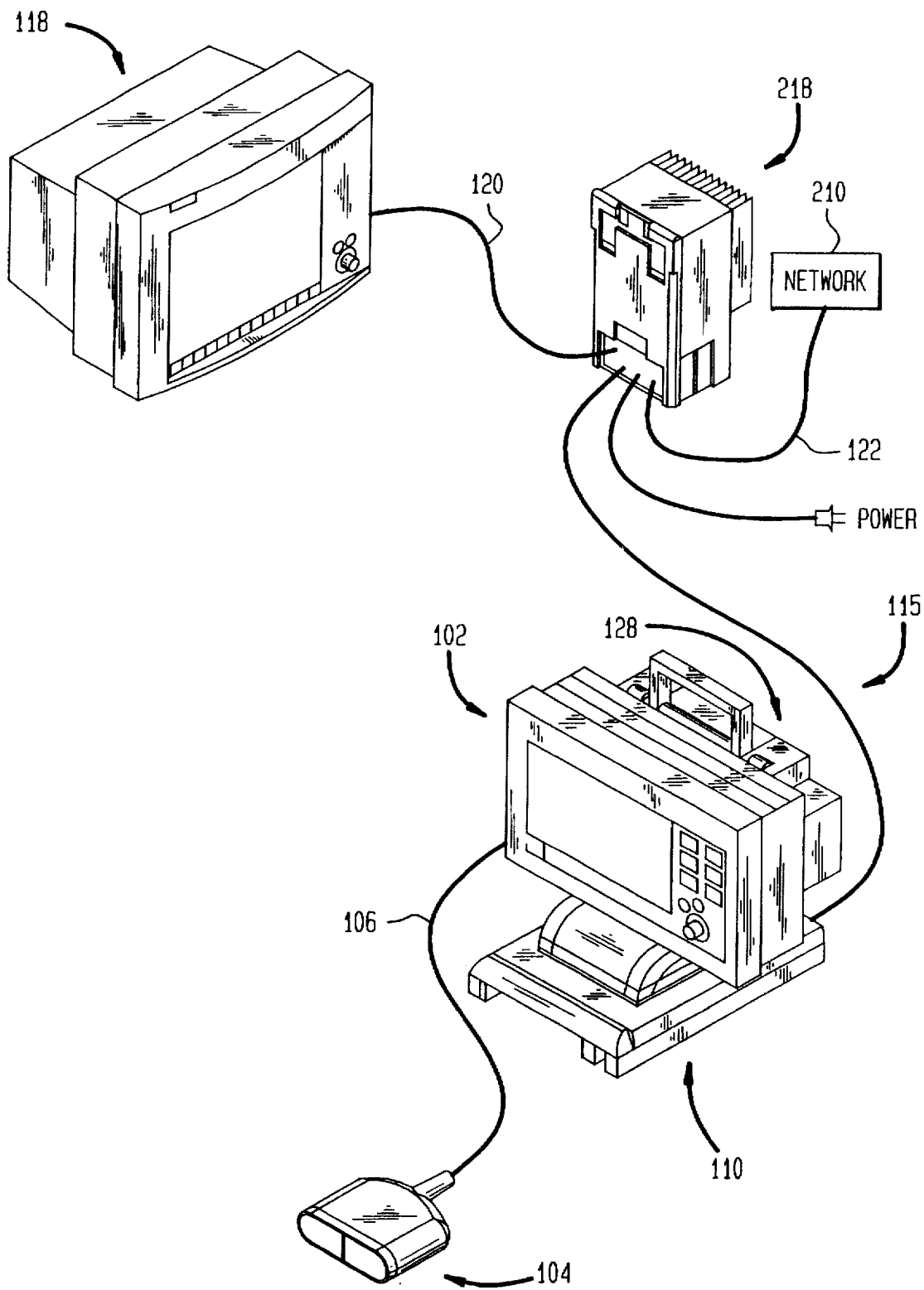
FIG. 2 illustrates an isometric view of the docking station platform and network connection wallbox shown in FIG. 1.

FIG. 2 shows an isometric view of an exemplary embodiment of the portable monitoring system 100 of FIG. 1, including docking station platform 110, a PSN 216, a bedside display 118 and a network 210. Docking station platform 110 is connected to PSN 216 by one or more cables 115 (which provides the connection 112 and 114 shown in FIG. 1). Portable monitor 102 is mounted on docking station platform 110, providing physical support, power, and communications to other devices either directly and/or via the network 210. As previously noted, monitor 102 acquires physiological data signals from a data acquisition pod 104. Illustratively, pod 104 provides data from ECG, SpO2 and Temperature sensors connected to a patient (not shown). A battery pack 128 is shown attached to the rear portion of the case of portable monitor 102 for providing power to monitor 102 during transport. Note: although only a single docking station platform is shown in the illustrated patient monitoring area, multiple docking station platforms could be used. Thus, in a hospital or other health care facility, docking station platforms 110 will be distributed throughout the facility in geographically separate areas, yet they will all be connected to one another for transfer of patient data therebetween via the wallboxes 116 an/or PSN's 216 and the system communication network 210.

FIG. 3 shows an exploded view of an exemplary docking station platform 110 to which portable devices, such as portable monitors 102, may be attached. Cable 115 of FIG. 2 is shown as cable 110m which carries electrical signals from PSN 216 to the portable monitor 102, through the docking station platform 110. A connector 110a at the docking station end of cable 110m is attached to a trolley 110g for controllable attachment to the portable device and a connector 110h at the other end of cable 110m interfaces with wallbox 116 using one of a variety of known LAN protocols.

A docking station top cover 110b not only functions as a protective cover, but also as a guide for mounting a portable device thereon. Cover 110b provides initial alignment using tapered outer edges and smooth rounded outer surfaces. Once aligned, contours along the outside top cover funnel the portable device into accurate final alignment, using positioning keys 110f. Keys 110f comprise one of more shaped indentation in the surface of top cover 110b and facilitate accurate alignment of a portable device with the docking station platform 110. Once positioned, flexible locking rail snaps 110d, flexibly protruding from the left and right sides on top cover 110b, fix the portable device to the docking station. Electrical connector 110a is then engaged with a corresponding electrical connector in the portable device by moving a lever arm 110c, which cams a docking station trolley 110g forward to mate with the corresponding connector in the portable device. The portable device is disengaged by moving lever arm 110c back to the initial position and release is accomplished by moving lever arm 110c an additional amount, using the reverse motion of its'camming action to retract the flexible locking rail snaps 110d from protruding from the sides of top cover 110b, thereby unlocking the portable device from docking station platform 110.

One technique for generating a signal for use by processor 130 to indicate that a portable monitor has been properly connected to a docking station, could be to use a sensor, such as a hall effect device, coupled to lever arm 110c to sense its position, and hence the proper coupling/uncoupling of the portable monitor.

Many variations of the forenoted mechanical configuration are possible. For example, when mounting a docking station platform 110 to a bed or IV pole, both of which are movable, it is desirable to provide a fixed position wallbox 116 for coupling the docking station with power, devices and networks outside of the room in which the docking station is located. A PSN 216 mounted on a wall is suitable for this purpose. Furthermore, different technologies may be used to transmit data between portable monitor 102 and docking station 111. Examples of these technologies include infra red and radio frequency transmission techniques. It is understood by one skilled in the art that several such technologies are possible to be used with or as a replacement for the connection (cable 110m) between the portable monitor and network 210. Furthermore, although portable monitor 102 is shown to have a display, in an alternative embodiment it may not have a display and instead a remote display is used.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

I claim:

1. A monitor system for acquiring medical data from at least one sensor adapted for attachment to a patient, comprising;

a communication network connecting at least two geographically separate patient monitoring areas;

a portable monitor adopted for coupling to the sensor for receiving and processing patient data signals from the sensor when the sensor is attached to the patient; and at least two patient monitor docking stations adapted to be selectively coupled to said portable monitor, with at least one docking station being located in each of the at least two geographically separate patient monitoring areas that are interconnected via said communication network, and connected for transmission of patient data received from the portable monitor to said communication network; wherein each docking station comprises:

coupling means for detachably coupling the portable monitor to the docking station;

signal transfer means for transferring patient-related data signals between the portable monitor and the docking station when the portable monitor is coupled to the docking station; and signal processing means for monitoring the patient-related data signals provided by the signal transfer means for developing a connection information signal when the portable monitor is coupled to the docking station, said connection information signal being applied for developing an alarm in the event that said signal processing means monitors that said portable monitor is not operating correctly.

2. The system of claim 1, wherein said connection information signal is applied to said communication network for developing said alarm at a geographic area which is separate from an area where said portable monitor is located.

3. The system of claim 2, wherein the geographic area separate from the area where said portable monitor is located includes a central monitor coupled to said network so as to receive patient-related data signals and a connection information signal from each of a plurality of portable monitors.

4. The system of claim 1, wherein said signal processing means comprises a central processing unit for monitoring the patient-related data signals for predetermined signal conditions indicative of normal operation of the portable monitor, and if said predetermined conditions are not monitored, developing said connection information signal, which is then applied to said communication network to indicate an alarm.

5. The system of claim 4, wherein said central processing unit includes means for periodically transmitting said connection information signal to said network.

6. The system of claim 1, wherein the docking station comprises first and second separate housings, with the coupling means and signal transferring means of the docking station being located in the first housing, and the signal processing means being located in the second housing.

7. A method for operating a monitor system for acquiring medical data from at least one sensor adapted for attachment to a patient, said system being distributed over at least two geographically separate patient monitoring areas and interconnected via a communication network, comprising the following steps:

receiving and processing patient data signals acquired from a patient by a portable monitor;

selectively coupling the portable monitor to one of at least two patient monitor docking stations, with at least one docking station being located in each of said at least two patient monitoring areas, and connected for transmission of patient data received from the portable patient monitor to said communication network;

transferring patient-related data signals between the portable monitor and the docking station when the portable monitor is coupled to the docking station;

monitoring the patient-related data signals transferred between the portable monitor and the docking station and developing a connection information signal when the portable monitor is coupled to the docking station; and developing an alarm in the event that said connection information signal indicates that said portable monitor is not operating correctly.

8. The method of claim 7, wherein said monitoring step applies said connection information signal to said network for developing said alarm at a geographic area which is separate from an area where said portable monitor is located.

9. The method of claim 7, wherein said monitoring step comprises monitoring the patient-related data signal for predetermined signal conditions indicative of normal operation of the portable monitor, and if said predetermined conditions are not monitored, causing said connection information signal which is applied to said communication network to indicate an alarm.

10. The method of claim 9, wherein said monitoring step periodically transmits said connection information signal to said communication network.

11. The method of claim 7, wherein said receiving step, selectively coupling step and said transferring step are all performed in a first housing of said docking station, and wherein said monitoring step is performed in a second housing of said docking station which is remote from said first housing.

\* \* \* \* \*